US00PP33260P2

(12) United States Plant Patent
Smith

(10) Patent No.: US PP33,260 P2
(45) Date of Patent: Jul. 13, 2021

(54) ***CHRYSANTHEMUM* PLANT NAMED 'CIFZ0080'**

(50) Latin Name: ***Chrysanthemum* x *morifolium***
Varietal Denomination: CIFZ0080

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/877,774

(22) Filed: May 19, 2020

(51) Int. Cl.
*A01H 5/02* (2018.01)
*A01H 6/14* (2018.01)

(52) U.S. Cl.
USPC ..... Plt./295

(58) Field of Classification Search
USPC ..... Plt./263.1, 284, 286, 287, 295
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new garden type *Chrysanthemum* plant named 'CIFZ0080' particularly distinguished by its medium to large size plant with round mound plant habit, a medium to large size decorative flower, yellow flower color and a natural season response of mid to late September.

1 Drawing Sheet

Figure 1:
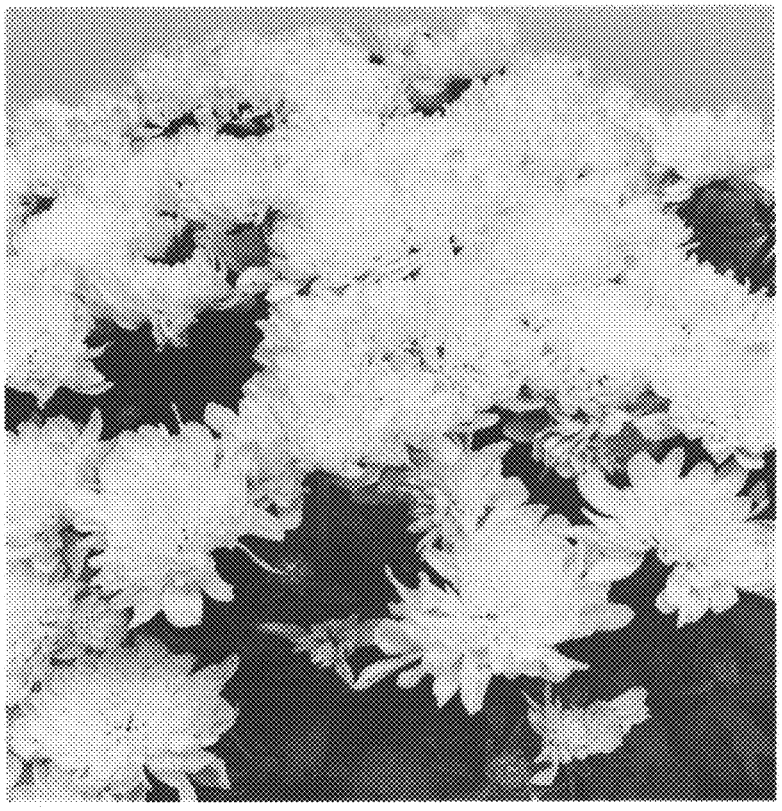

Latin name of the genus and species of the plant claimed: *Chrysanthemum* x *morifolium*.

Varietal denomination: 'CIFZ0080'.

BACKGROUND OF THE NEW PLANT

The present invention comprises a new *Chrysanthemum*, botanically known as *Chrysanthemum* x *morifolium*, and hereinafter referred to by the variety name 'CIFZ0080'.

'CIFZ0080' is a product of a planned breeding program. The new cultivar has a medium to large size plant with round mound plant habit, a medium to large size decorative flower, yellow flower color and a natural season response of mid to late September.

'CIFZ0080' originated from a cross made on Aug. 22, 2008 in Tenjo, Colombia. Seeds were sown in June 2015 in Gilroy, Calif. and 'CIFZ0080' was selected from the resulting population on October 22 in Monroeville, N.J.

The female parent was the variety 'Yomildred', U.S. Plant Pat. No. 21,187.

TABLE 1

Characteristics of the female parent compared to 'CIFZ0080':

| Trait | 'CIFZ0080' | 'Yomildred' |
|---|---|---|
| Natural response: | 4.5 weeks faster | 4.5 weeks slower |
| Blackcloth response: | ½ week faster | ½ week slower |
| Flower size: | Larger | Smaller |
| Flower color: | Yellow | White |
| Flower type: | Similar | Similar |
| Plant size: | Taller/less wide | Shorter/wider |
| Plant habit: | Similar | Similar |

The male parent was 'Semone', not patented.

TABLE 2

Characteristics of the male parent compared to 'CIFZ0080':

| Trait | 'CIFZ0080' | 'Semone' |
|---|---|---|
| Natural response: | 2 weeks faster | 2 weeks slower |
| Black cloth response: | 1 week faster | 1 week slower |
| Flower size: | Larger | Smaller |
| Flower color: | Similar | Similar |
| Flower type: | Less disc florets | More disc florets |
| Plant size: | Smaller | Larger |
| Plant habit: | Similar/shorter | Similar/taller |

The first act of asexual reproduction of 'CIFZ0080' was accomplished when vegetative stem cuttings were propagated from the initial selection in January 2016 in Mebane, N.C.

BRIEF SUMMARY OF INVENTION

Horticultural examination of plants grown from cuttings of the plant initiated in January 2016 and continuing thereafter, has demonstrated that the combination of characteristics as herein disclosed for 'CIFZ0080' are firmly fixed and are retained through successive generations of asexual reproduction.

'CIFZ0080' has not been observed under all possible environmental conditions. The phenotype may vary significantly with variations in environment such as temperature, light intensity and day length.

A Plant Breeder's Right for this cultivar has not yet been applied for. 'CIFZ0080' has not been made publicly available prior to the effective filing date of this application, notwithstanding any disclosure that may have been made less than one year prior to the effective filing date of this application by the inventor or another who obtained 'CIFZ0080' directly from the inventor.

The following traits have been repeatedly observed and are determined to be basic characteristics of the new variety.

The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0080' with colors being as true as possible with an illustration of this type.

Figure 2:
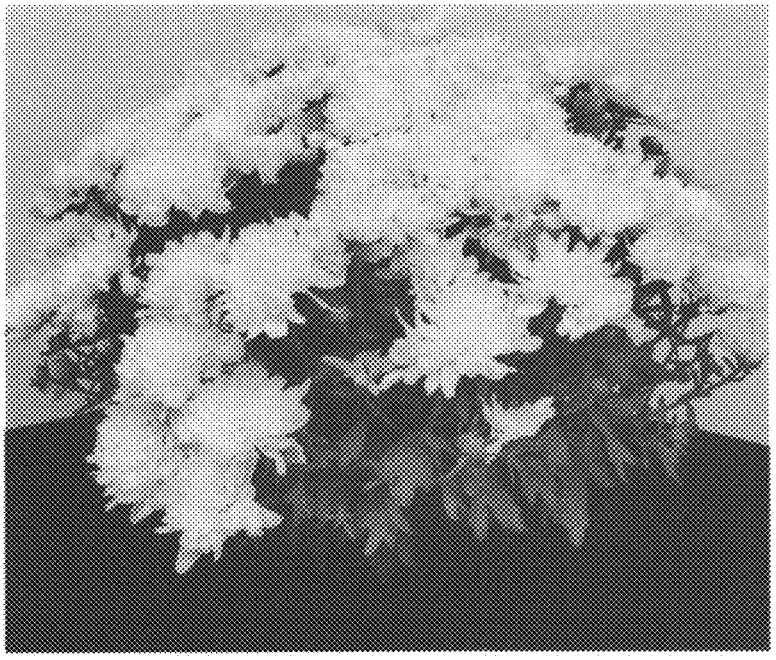

The photographic drawing shows in FIG. 1 a close view of flower of the new variety and in FIG. 2 a flowering plant from an outdoor trial.

The aforementioned photographs, FIG. 1 as well as FIG. 2, were taken in September 2019 both showing a plant from the same black cloth indoor trial in Gilroy, Calif. These plants were about 10 weeks of age. One rooted cutting per pot had been planted in a one gallon pot, not pinched in week 24, and black clothed from week 25. Plants started flowering the end of August.

DETAILED BOTANICAL DESCRIPTION

The measurements were taken in Gilroy, Calif., in September 2019, on the plants from the aforementioned trial.

Color references are made to The Royal Horticultural Society Colour Chart (R.H.S.) 2015.

DIFFERENCES BETWEEN THE NEW VARIETY 'CIFZ0080' AND TWO MOST SIMILAR VARIETIES

TABLE 3

| Trait | 'CIFZ0080' | 'Yomary', U.S. Plant Pat. No. 18,993 |
|---|---|---|
| Natural response - bud color: | Similar | Similar |
| Natural response - flowers: | 1 week faster | 1 week slower |
| Black cloth response: | ½ week slower | ½ week faster |
| Flower size: | Similar | Similar |
| Flower color: | Similar | Similar |
| Plant size: | Similar | Similar |
| Plant habit: | More full | Less full |
| Flowering uniformity: | More Uniform | Less Uniform |

TABLE 4

| Trait | 'CIFZ0080' | 'Gedi Three Pyel', U.S. Plant Pat. No. 17,000 |
|---|---|---|
| Natural response: | Similar | Similar |
| Black cloth response: | 1.5 weeks faster | 1.5 weeks slower |
| Flower size: | Larger | Smaller |
| Flower color: | Similar | Similar |
| Flower type: | Less disc florets | More disc florets |
| Plant size: | Similar | Similar |
| Plant habit: | More mounded | More upright |
| Flowering uniformity: | More Uniform | Less Uniform |

Plant:

*Form, growth and habit.*—Herbaceous garden-type, stems Upright and outwardly spreading, freely branching, strong and moderately vigorous growth habit.

*Plant height (above soil).*—15-18 cm.

*Plant height (inflorescence included).*—19-22 cm.

*Plant width.*—40 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137C.

*Mature leaf, color, upper surface.*—RHS NN137A.

*Mature leaf, color lower surface.*—RHS NN137C.

*Length.*—5.1 cm.

*Width.*—4.0 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Many.

*Depth of margin indentations.*—Shallow.

*Leaf length terminal lobe relative to total leaf length.*—Terminal lobe is ½ to ⅓ the length of the total leaf=Medium.

*Leaf depth lower lateral sinus.*—Shallow.

*Texture, upper surface.*—Pubescent.

*Texture, lower surface.*—Pubescent.

*Color of veins, upper surface.*—RHS 138B.

*Color of veins, lower surface.*—RHS 138A.

*Pattern of veining.*—Palmate.

*Petiole color.*—RHS 137A.

*Petiole length.*—1.0-1.1 cm.

*Diameter.*—0.2-0.3 cm.

*Texture.*—Pubescent.

*Presence of stipules.*—Yes.

*If present, size of stipules.*—2 mm wide and 3 mm long.

Stem:

*Quantity of main branches per plant.*—6-8.

*Color of stem.*—RHS 138A.

*Length of stem.*—8.0-9.0 cm.

*Diameter.*—0.5 cm.

*Length of internodes.*—2.5-3.0 cm.

*Texture.*—Pubescent.

*Color of peduncle.*—RHS 138A.

*Length of peduncle.*—4.0-4.5 cm.

*Peduncle diameter.*—0.3 cm.

*Texture.*—Pubescent.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 6 weeks.

*Natural season flowering.*—Mid to late September.

*Quantity of inflorescences per plant.*—140-150 with many small buds developing.

*Lastingness of individual blooms on the plant.*—About five weeks from first color.

*Fragrance.*—Slightly spicy.

Bud (when showing color):
*Color*.—RHS 8A.
*Length*.—0.8-0.9 cm.
*Width*.—1.0-1.1 cm.
*Shape*.—Oblate.
Immature inflorescence (at moment of opening):
*Diameter*.—2.0-2.5 cm.
*Color of ray florets, upper surface*.—RHS 9B; darkest at apex.
*Color of ray florets, lower surface*.—RHS 8B.
Mature inflorescence:
*Diameter*.—4.6 cm.
*Depth*.—1.4 cm.
*Total diameter of disc*.—0.3 cm to no disc present.
*Receptacle color*.—RHS 9A.
*Receptacle height*.—0.6 cm.
*Receptacle diameter*.—3.0 cm.
*Length of corolla tube*.—Medium.
Ray florets:
*Average quantity of florets*.—140-150 in several whorls.
*Color of florets, upper surface*.—RHS 9A; darker at apex.
*Color inner surface*.—RHS 9A.
*Length*.—2.7 cm.
*Width/diameter*.—0.5-0.6 cm.
*Shape*.—Elliptical.
*Apex shape*.—Mostly obtuse and dentate.
*Base shape*.—Tube.
*Margin*.—Entire. Small incisions may be present at tip.
*Margin*.—Type of rolling: Weakly involute.
*Texture, upper surface*.—Papillate.
*Lower surface*.—Papillate.
*Ribs present*.—Yes.
*Number of keels*.—0.
Disc florets:
*Number of disc florets*.—Up to 200, may not be present in all flowers.
*Width*.—Up to 0.5 cm.
*Length*.—3.0 cm.
*Color*.—RHS 1B; 144B at base.
Inflorescence (at moment of senescence):
*Color of ray florets, upper surface*.—Outer layers; RHS 9A; darker at apex.
*Color of ray florets, lower surface*.—RHS 9A.
Phyllaries:
*Quantity*.—20-25.
*Color, upper surface*.—RHS 143C.
*Color, lower surface*.—RHS 143A.
*Length*.—0.6 cm.
*Width*.—0.1-0.2 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.
Reproductive organs:
*Pistil*.—One.
*Length*.—0.4 cm.
*Style color*.—RHS 150C.
*Style length*.—0.3 cm.
*Stigma color*.—RHS 7D.
*Stigma shape*.—Bi-parted.
*Ovary color*.—RHS 145C.
*Ovary length*.—0.2 cm.
*Ovary width*.—0.1 cm.
Androecium:
*Stamens*.—1, found on only disc florets.
*Color of filaments*.—RHS 2B.
*Length filaments*.—0.2 cm.
*Anther color*.—RHS 13A.
*Anther length*.—0.2 cm.
*Anther shape*.—Oval to club shaped.
*Color of pollen*.—RHS 13A.
*Pollen amount*.—Moderate.
*Fertility/seed set*.—Has not been determined to date.
*Disease/pest resistance*.—Has not been determined to date.
*Hardiness*.—Has not been determined to date.

What is claimed is:

1. A new and distinct variety of *Chrysanthemum* plant named 'CIFZ0080' substantially as illustrated and described herein.

* * * * *